United States Patent [19]

Rao

[11] Patent Number: 5,014,545
[45] Date of Patent: May 14, 1991

[54] APPARATUS FOR DETERMINING FLOW BEHAVIOR INDEX

[75] Inventor: Sundar M. Rao, Seaford, Del.

[73] Assignee: E. I. du Pont de Nemours and Company, Wilmington, Del.

[21] Appl. No.: 587,152

[22] Filed: Sep. 19, 1990

[51] Int. Cl.$^5$ ........................................... G01N 11/04
[52] U.S. Cl. ........................................................ 73/55
[58] Field of Search ............................. 73/55, 56, 53

[56] References Cited

U.S. PATENT DOCUMENTS

| | | | |
|---|---|---|---|
| 3,024,643 | 3/1962 | Jones, Jr. | 73/55 |
| 3,116,630 | 1/1964 | Piros | 73/55 |
| 3,138,950 | 6/1964 | Welty et al. | 73/55 |
| 3,548,638 | 12/1970 | Uchida et al. | 73/55 |
| 3,559,464 | 2/1971 | Woust et al. | 73/55 |
| 3,938,369 | 2/1976 | de Bok | 73/55 |
| 4,213,747 | 7/1980 | Friedrich | 73/55 |
| 4,726,219 | 2/1988 | Pearson et al. | 73/53 |
| 4,735,779 | 4/1988 | Handel | 422/105 |
| 4,792,908 | 12/1988 | Brantley | 523/303 |
| 4,817,416 | 4/1989 | Blanch et al. | 73/55 |

FOREIGN PATENT DOCUMENTS

| | | | |
|---|---|---|---|
| 24559 | 12/1970 | Japan | 73/55 |
| 155740 | 9/1984 | Japan | 73/55 |
| 211542 | 9/1987 | Japan | 73/55 |
| 657696 | 9/1951 | United Kingdom | 73/55 |

Primary Examiner—Hezron E. Williams
Assistant Examiner—Joseph W. Roskos

[57] ABSTRACT

An apparatus for on-line determination and control of the Flow Behavior Index of a molten polymer stream are disclosed along with methods for using the Index as a means for monitoring and controlling polymer quality. In particular, the Index may be used to monitor and control on-line the levels of branching in the polymer and the polymer's molecular weight distribution.

3 Claims, 3 Drawing Sheets

APPARATUS FOR DETERMINING FLOW BEHAVIOR INDEX

This is a division of application Ser. No. 07/463,897, filed Jan. 9, 1990, U.S. Pat. No. 4,992,487.

TECHNICAL FIELD

The present invention relates generally to the on-line determination of the Flow Behavior Index of a molten polymer and the use of this Index to determine and control various properties of the polymer such as the level of branching and the molecular weight distribution.

BACKGROUND OF THE INVENTION

In making and using synthetic polymers, it is necessary to know and control the viscosity of the molten polymer stream within desired limits to maintain process continuity and to help control product quality and uniformity. On-line viscometers are known which divert a portion of a melted polymer stream through an instrument which measures, at a given temperature, the pressure drop across a restriction in the flow path under a particular initial pressure or at a particular flow rate. Using these values, the viscosity of the polymer may be calculated.

While viscosity measurements at a single, low shear rate are sufficient to control polymer processes where the quality of the polymer is consistent, these measurements are of questionable value when polymerization results in excessive branching of the polymer chains or in changes in molecular weight distribution. At low shear rates such branching may not have much impact on viscosity, but at high shear rates it does have a significant impact on viscosity. In polymer processes where final product uniformity is determined by high shear processing, such as fiber forming, viscosity measurements at multiple shear rates and interpretations of results becomes important in order to determine whether the branching level and the molecular weight distribution are within established desired limits. Heretofore the branching level and the molecular weight distribution, if measured at all, have been measured off-line, leading to costly delays and inefficiencies in the event such off-line testing indicated the need for correction.

SUMMARY OF THE INVENTION

Using a variation of these on-line viscometers, it has now been found that further useful viscosity-related diagnostic information for a molten polymer can be obtained on-line by determining the polymer's Flow Behavior Index (hereinafter "FBI"). The FBI may be determined by successively diverting more than one small quantity of the molten polymer from its path to a capillary of known length and diameter, moving each small quantity through the capillary at a different controlled rate and at a constant temperature, measuring the pressure drop across the capillary at each controlled rate, using the controlled rates, pressure drops, capillary length and diameter to calculate shear rate and shear stress, and comparing shear rate and shear stress to determine the FBI. Specifically the FBI may be defined using such data as the slope of a best-fit straight line through the data points of shear stress plotted as a function of shear rate on a log-log graph.

Comparing the FBI with known values for a given polymer provides an indication of the level of branching in the polymer or its molecular weight distribution. To the extent that this level is outside desired limits, a correction can be made either by altering the rheological properties of the polymer stream by varying polymer process conditions such as temperature or by mixing in additives to the polymer itself.

In this fashion the FBI can be used to determine and control certain physical properties such as branching level, molecular weight distribution, and what is sometimes known as "shear-thinning", i.e. the change in viscosity as a function of shear rate.

A first embodiment of the present invention relates to a process to specifically determine the FBI of a molten polymer moving at a controlled temperature along a prescribed path. This process comprises the sequential steps of:
  (a) successively diverting more than one small quantity of the molten polymer from the path to a capillary of known length and diameter;
  (b) moving each small quantity through the capillary at a different controlled rate and at a constant temperature;
  (c) measuring the pressure drop across the capillary at each controlled rate;
  (d) using the controlled rates, pressure drops, capillary length and diameter to calculate shear rate and shear stress;
  (e) comparing shear rate and shear stress to determine a Flow Behavior Index.

In a subsequent embodiment the FBI can be determined and controlled by varying the rheological properties of the molten polymer being processed.

A further embodiment relates to a process for using the FBI to control to within certain predefined limits a physical property of a molten polymer having certain rheological properties, said polymer moving at a controlled temperature along a prescribed path, comprising the sequential steps of:
  (a) successively diverting more than one small quantity of the molten polymer from the path to a capillary of known length and diameter;
  (b) moving each small quantity through the capillary at a different controlled rate and at a constant temperature;
  (c) measuring the pressure drop across the capillary at each controlled rate;
  (d) using the controlled rates, pressure drops, capillary length and diameter to calculate shear rate and shear stress;
  (e) comparing shear rate and shear stress to determine the Flow Behavior Index;
  (f) correlating the Flow Behavior Index with the predefined limits to determine the physical property of the polymer; and
  (g) varying the rheological properties of the molten polymer to bring the physical property within the predefined limits.

A still further embodiment of the invention involves an apparatus for determining the FBI of a molten polymer moving in a process at a controlled temperature along a prescribed path, the apparatus comprising:
  (a) a capillary of known length and diameter in line with the prescribed path;
  (b) means for successively diverting more than one small quantity of the molten polymer from the path to the capillary;

(c) means for moving each small quantity through the capillary at a different controlled rate and at a constant temperature;

(d) means for measuring the pressure drop across the capillary at each controlled rate;

(e) means for using the controlled rates, pressure drops y length and diameter to calculate shear rate and shear stress;

(f) means for comparing shear rate and shear stress to determine a Flow Behavior Index.

DETAILED DESCRIPTION OF THE INVENTION

Figure 1:
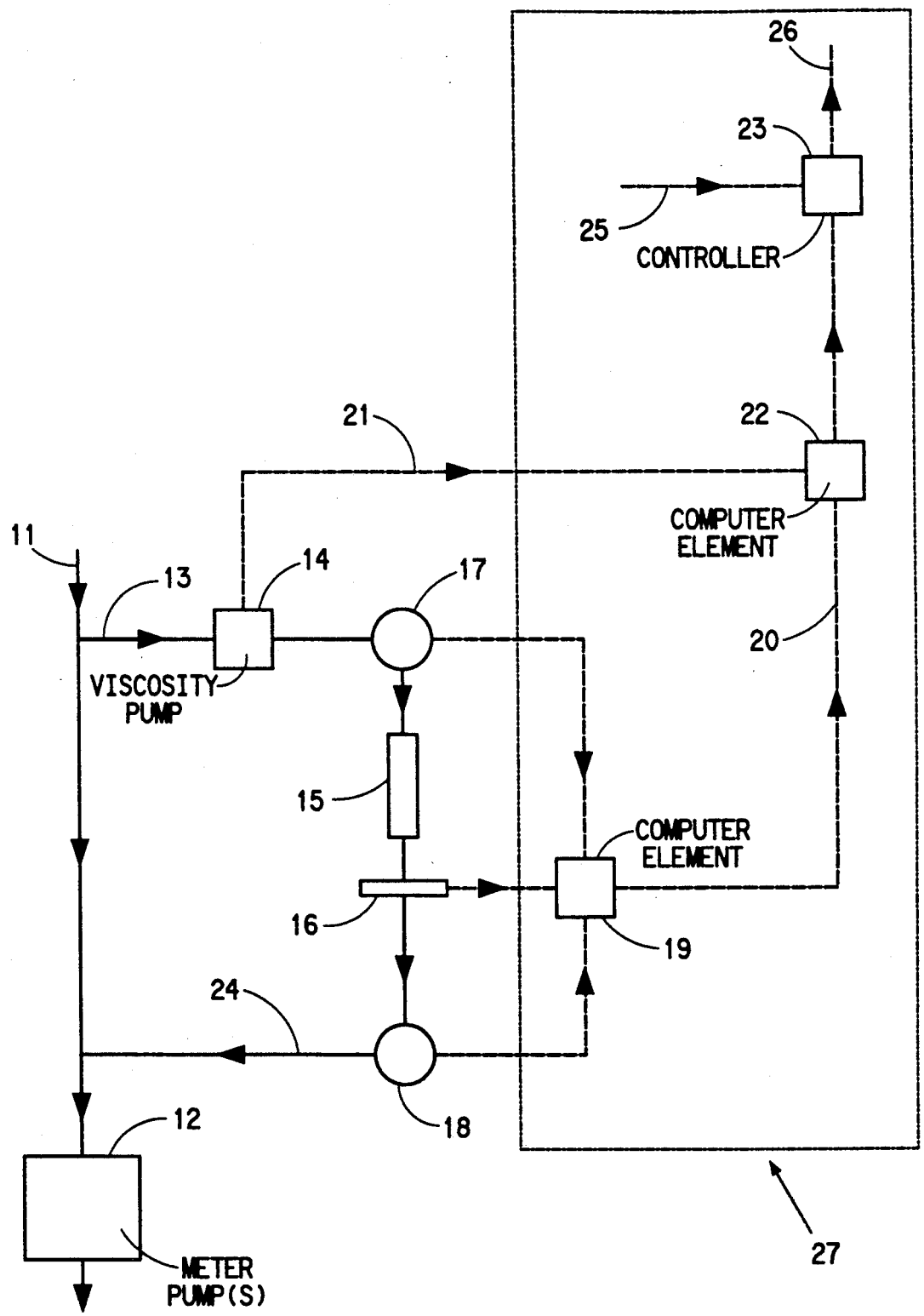
FIG. 1 is a schematic of a polymer process showing on-line measurement of polymer viscosity and which is also capable of determining the FBI of the polymer.

This invention involves an advancement over the on-line measurement of the viscosity of a molten polymer stream moving along a prescribed path at a controlled process temperature. Customarily viscosity is measured by diverting a small quantity of the molten polymer from the polymer stream, and forcing it, by for example a pump, through a capillary of known length and diameter at a constant temperature and at a controlled rate. By measuring the pressure drop across the capillary at the controlled rate and constant temperature, the viscosity can be calculated and appropriate adjustments made.

As described more fully hereinafter, it has now been found that by repeating this process at different controlled rates, pressure drops for each controlled rate can be determined. These pressure drops can then be used, along with the capillary dimensions, to calculate shear rate and shear stress values which can then be plotted on a log-log graph. The slope of the best-fit straight line drawn through those points is the Flow Behavior Index (FBI).

Once the FBI is determined, the process operator can vary the rheological properties of the polymer stream to bring the FBI to within predefined, desired limits and to subsequently maintain it in such range. Since the FBI is a rheological property of the molten polymer, it can be controlled by making adjustments used to control other rheological properties such as viscosity. Such methods include varying the controlled temperature of the polymer stream, the FBI being inversely related to the temperature of the molten polymer, and the mixing of additives with the molten polymer. Useful additives may include well-known chain terminators and branching agents. In this manner the FBI itself may be used to monitor and control polymer rheology.

Since the molten polymer's rheology is related to the polymer's physical properties, the FBI may be used as a means for controlling those physical properties which correlate well with rheological properties. One such physical property is the level of branching of the polymer. Branching, which may or may not involve cross-linking of the polymer molecules, must be controlled as it can impact such properties as dyeability and spinning behavior when the molten polymer is spun into synthetic fibers. Branching can be an indicator of the level of impurities in the polymer, in which case purification of the polymer may be required to make a suitable correction, but branching may also be caused by process conditions such as temperature fluctuations. It is desirable to monitor and control process-related branching so as to maintain a uniform degree of branching from lot-to-lot of polymer. This is often done by the use of small quantities of branching agents.

High levels of branching tend to reduce the FBI, so that on-line readings showing an unacceptably low FBI or a diminishing FBI may be an indication of increased branching. Conversely, high FBI or increasing FBI may be an indication of decreased or insufficient branching. The level of branching may then be altered by changing the controlled temperature of the molten polymer, a change which also alters the polymer's rheology and adjusts the FBI. Similarly additives may be mixed into the molten polymer to vary the rheological properties of the melt and return the branching level to the normal predefined limits. Such additives include branching agents, such as bis-hexamethyl methylene triamine (BHMT), and other additives generally referred to as controlled rheology agents. A more complete discussion of such agents may be found in *Modern Plastics Mid-October Encyclopedia,*, Issue No. 90, page 98, which is hereby incorporated by reference into this disclosure.

An additional property which can be monitored and adjusted due to its correlation with FBI is the molecular weight distribution of the polymer. Depending on the polymer being processed and the application involved, broad or narrow ranges of molecular weight distribution are often desirable. Polymer properties such as shear viscosity, extensional viscosity, intrinisic viscosity, extrudate swell, melting and crystallization temperatures, flexural modulus, impact strength, and tensile stress have all been correlated with molecular weight distribution; hence control of the polymer's molecular weight distribution can provide a means to monitor and control such properties. Since the FBI varies with changes in molecular weight distribution, with this invention molecular weight distribution can now be monitored on-line for deviations from established limits. Such deviations can then be corrected by mixing additives such as chain terminators and other controlled rheology agents into the molten polymer stream. Control of molecular weight distribution is particularly important when working with polymers formed by addition reactions, such as polyethylene and polypropylene. In such cases, additives like peroxides may be mixed with the molten polymer to act as chain terminators and thus control molecular weight distribution.

The processes of this invention are thought to be useful when working with all types of polymers, including but not limited to polyolefins, polyamides, polyesters, and copolymers thereof. Similarly, the processes are not limited by the use to be made of the molten polymer stream. It is expected that the techniques described herein will have value as a polymer process control tool in any application where rheological properties may be measured and where polymer uniformity is important.

The apparatus of this invention is an apparatus for determining the FBI of a molten polymer moving at a controlled temperature along a prescribed path. The apparatus is comprised of:
(a) a capillary of known length and diameter in line with the prescribed path;
(b) means for successively diverting more than one small quantity of the molten polymer from the path to the capillary;
(c) means for moving each small quantity through the capillary at a different controlled rate and at a constant temperature;
(d) means for measuring the pressure drop across the capillary at each controlled rate;
(e) means for using the controlled rates, pressure drops, capillary length and diameter to calculate shear rate and shear stress;
(f) means for comparing shear rate and shear stress to determine the Flow Behavior Index.

The preferred means for measuring the pressure drop across the capillary at each controlled rate is a viscometer, and the preferred means for moving each small quantity through the capillary at a different controlled rate (and at a constant temperature) is a variable-speed drive connected to a pump.

Referring to FIG. 1, molten polymer from a source not shown is delivered through pipe 11 on its way to one or more meter pumps 12 and then, for example, to spinnerets for extruding polymeric filaments. A small portion of the polymer is diverted through pipe 13 to viscometer pump 14 which forces the polymer at a controlled rate through capillary 15. Thermocouple 16 detects the temperature of the polymer at the capillary and pressure sensors 17 and 18 detect the polymer pressures before and after the capillary, respectively. They transmit their readings to element 19 within computer 27 which determines the difference in pressure across the capillary.

Using the differential pressure reading 20 and the capillary length and diameter, the shear rate is calculated by computer element 22 from Equation #2 below. Since the pump speed is directly proportional to the capillary throughput of a polymer at constant temperature, the computer can also readily determine the throughput through the capillary from the pump speed 21. The throughput can, in turn, be used to compute the shear rate as shown in Equation #3 below.

Pipe 13, pump 14, capillary 15 and return pipe 24 should be maintained at constant temperature by suitable insulation and electrical heating. The accuracy of the measurement may be improved by installing one or more static mixers in pipe 13.

By adjusting the drive signal to the motor driving pump 14, the speed of the pump can be varied between 5 and 40 RPM, thereby getting a 8× increase in shear rate. This may be done manually, preferably in increments of 5 RPM. This can also be done by a programmable logic controller (such as an Allan Bradley PLC 3) or by a Honeywell Distributed Control System TDC 3000.

The data are used to calculate a Flow Behavior Index, which for non-Newtonian flow is:

$$\tau_w = K\Phi^n \quad (1)$$

where
$\tau_w$ = shear stress
$\Phi$ = shear rate
and n = Flow Behavior Index

The differential pressure $\Delta P$, measured with the viscometer, is converted to $\tau_w$ by:

$$\tau_w = D_o \frac{\Delta P}{4L} \quad \text{(Equation \#2)}$$

where
$D_o$ = capillary diameter
and L = capillary length
The shear rate $\Phi$ is calculated by:

$$\Phi = \frac{32Q}{\pi D_o^3} \quad \text{(Equation \#3)}$$

where
Q = throughput through the capillary
and $D_o$ = capillary diameter

The shear stress ($\tau_w$) may then be plotted as a function of shear rate ($\Phi$) on a log-log graph with the slope of the resulting best-fit straight line being the FBI.

Figure 2:
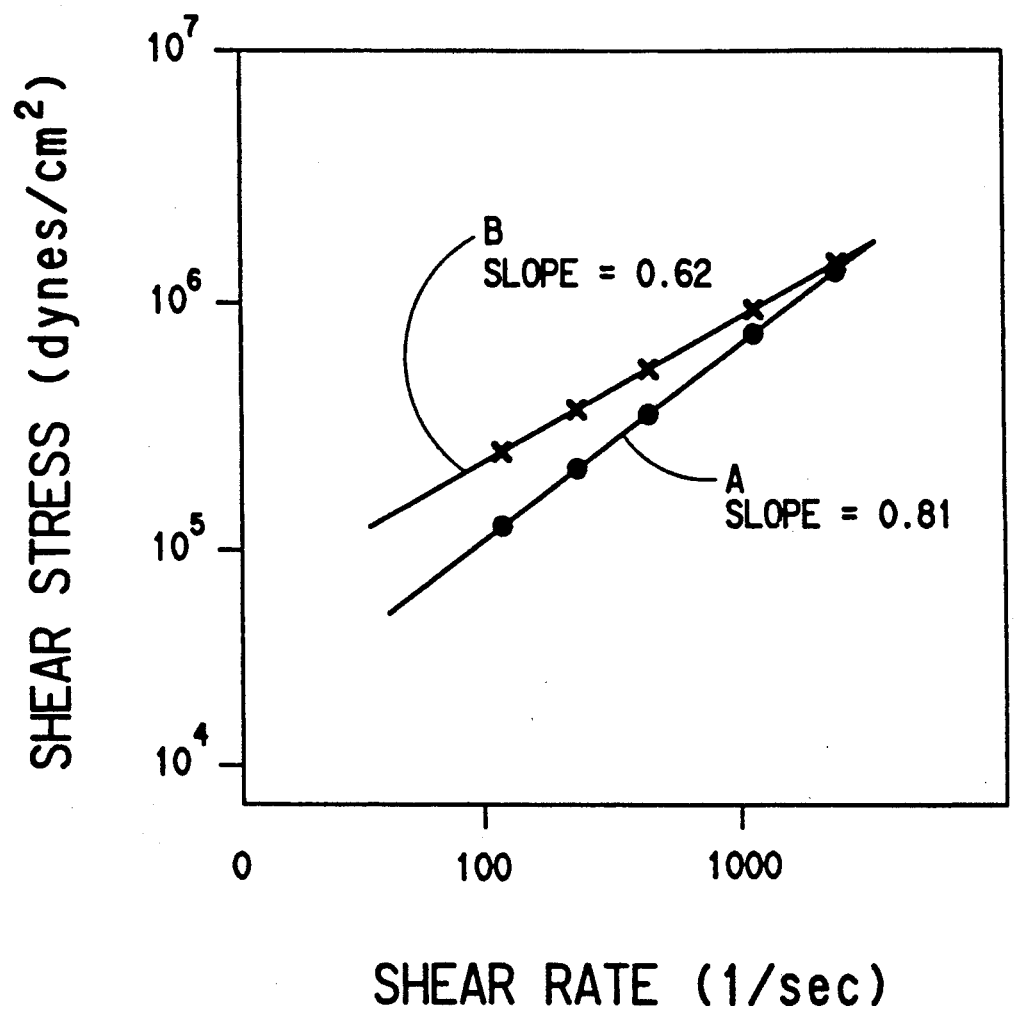
FIG. 2 is a graph showing the relationship between shear rate in reciprocal seconds and shear stress in dynes/cm$^2$ for two nylon 6,6 polymers with different branching levels, the slope of each line shown being the FBI for that polymer.

FIG. 2 shows two plots of shear stress in dynes per square centimeter on the vertical axis and shear rate in sec.$^{-1}$ on the horizontal axis, both on logarithmic scales. Control Plot A, having a slope (i.e. FBI) of 0.81, shows data points for a nylon 6,6 polymer with essentially no branching. Plot B, having a slope (i.e. FBI) of 0.62, shows values for the same nylon 6,6 polymer with substantial branching caused by the addition of the branching agent BHMT to the polymer in concentrations of 15 mg/$10^6$ g. This demonstrates the use of the FBI to monitor branching levels.

In addition to detecting polymer branching and variation in molecular weight distribution, the process and apparatus of this invention can also detect undesirable effects of additives such as improper dispersion of delustering or coloring pigments, undesirable reactions of additives with the polymer, etc., which cannot be thoroughly characterized by a viscosity measurement made at only one shear rate. It has been found that coloring pigments can significantly affect the rheological properties of polymers, including particulary nylon 6,6. FBI values for such pigmented polymers are correspondingly changed, and the FBI values can be significantly higher than those for the same polymer without pigment. Through routine experimentation FBI levels indicating acceptable levels of pigment and proper pigment dispersion can be determined, thus permitting on-line monitoring and control of polymer pigmentation using the methods and apparata of this invention. The effect of delustering pigments may be similarly monitored and controlled. Copolymers may also be characterized more thoroughly and accurately, particularly for completeness of blending of melt-blend copolymers.

As depicted schematically on FIG. 1, the present device may also activate corrective control of the polymer process by determining whether the slope of the plot deviates from a desired condition, feeding the signal into an additional controller 23 which receives a signal (Honeywell Distributed Control System or equivalent) 25 and sends a further signal 26 to make a correction to the polymer-making process, such as polymer temperature. An additional signal may also be sent to the flake makeup process.

EXAMPLES

FBI values for two different nylon 6,6 polymers were calculated as follows:

EXAMPLE 1

A nylon 6,6 polymer in flake form was melted in a screw-melter and flowed through a transfer line at a controlled temperature of 290° C. to a spinning machine for extrusion into filaments. An on-line drop-leg viscometer as shown schematically in FIG. 1 and described above was used to measure the throughput through a capillary and the pressure drop across the capillary at various viscometer pump speeds as the polymer moved through the transfer line. A 1S-3C Zenith gear pump was used, and the pump speeds were varied from 10 RPM to 40 RPM. Throughput through the capillary (which was 0.5 inches (1.27 cm) in length and had a diameter of 0.093 inch (0.236 cm)) was determined, and the pressure drop across the capillary was measured. Shear stress and shear rate were then calculated using Equations #2 and #3, respectively.

| Pump (RPM) | Capillary Throughput (ft.$^3$/sec) | Pressure Drop (psi) | Shear Rate (sec$^{-1}$) | Shear Stress (lbs/in.$^2$) |
|---|---|---|---|---|
| 40 | 4.62 × 10$^{-5}$ | 800 | 1008 | 37.2 |
| 30 | 3.46 × 10$^{-5}$ | 655 | 757 | 30.40 |
| 20 | 2.31 × 10$^{-5}$ | 490 | 504 | 22.78 |
| 10 | 1.15 × 10$^{-5}$ | 290 | 252 | 13.48 |

Figure 3:
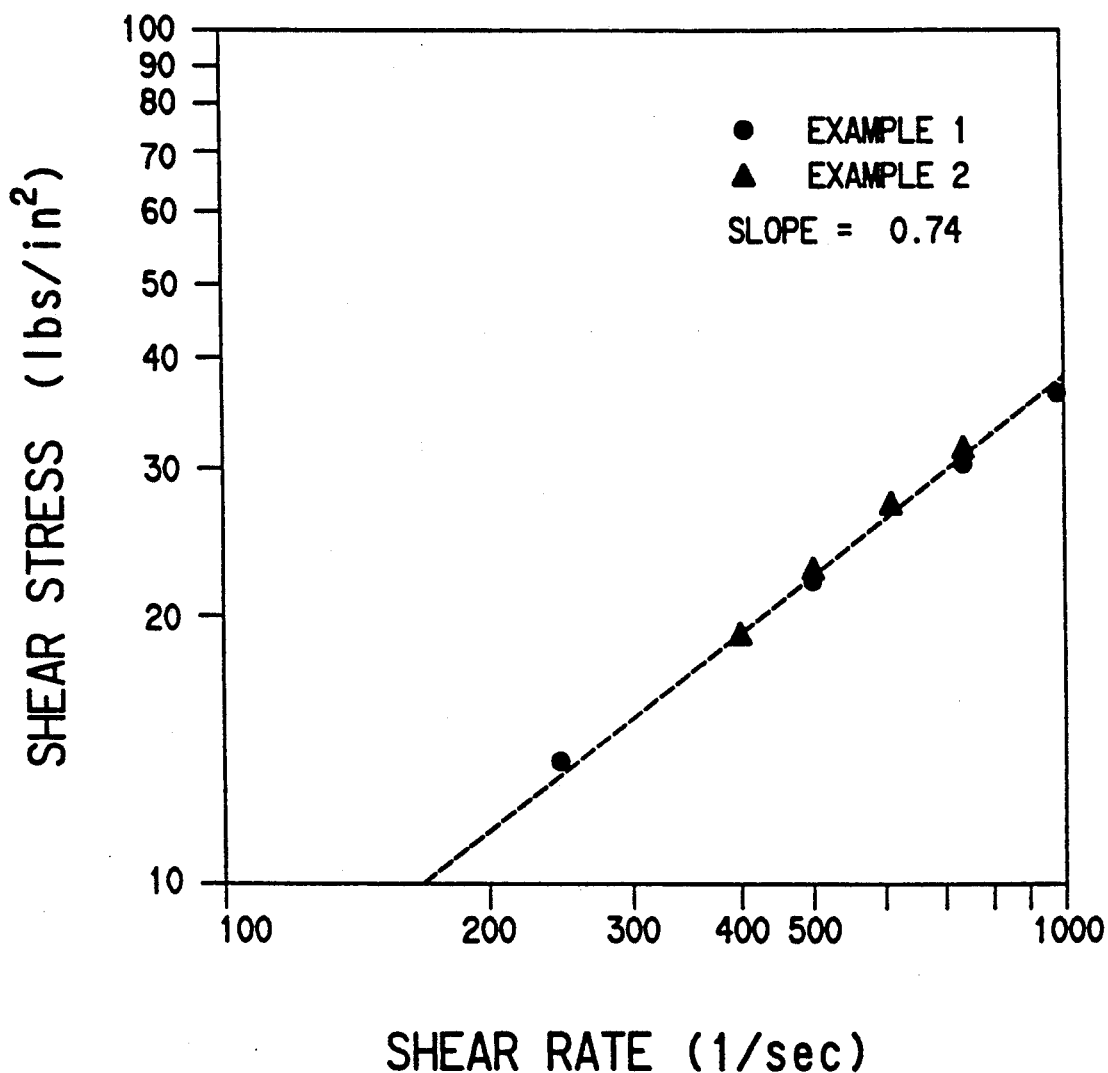
FIG. 3 is a graph showing the relationship between shear rate in reciprocal seconds and shear stress in lbs/in$^2$ for two different nylon 6,6 polymers with virtually identical branching levels.

When plotted on a log-log graph as shown in FIG. 3, the slope of the best fit straight line through these data points gave an FBI value of 0.74.

EXAMPLE 2

A similar evaluation was made on a second nylon 6,6 polymer also being transferred from a screw melter to a spinning machine. In this case a 1S-5C viscometer pump was used and the capillary again had a length of 0.5 inches (1.27 cm) and a diameter of 0.093 inches (0.236 cm). As the pump speed was varied, the throughputs were determined and pressure drops were measured. Shear rate and shear stress values were again calculated as shown below:

| Pump Speed (RPM) | Capillary Throughput (ft$^3$/sec) | Pressure Drop (psi) | Shear Rate (sec$^{-1}$) | Shear Stress (lbs/in.$^2$) |
|---|---|---|---|---|
| 18 | 3.46 × 10$^{-5}$ | 670 | 757 | 31.16 |
| 15 | 2.89 × 10$^{-5}$ | 590 | 630 | 27.44 |
| 12 | 2.31 × 10$^{-5}$ | 490 | 504 | 22.78 |
| 10 | 1.92 × 10$^{-5}$ | 430 | 420 | 19.99 |

When plotted on a log-log graph (see FIG. 3), the slope of the best fit straight line through these data points also gave an FBI value of 0.74, indicating comparable rheological properties, and comparable branching levels to the polymer evaluated in Example 1. Since it is known that an FBI value of 0.81 for non-pigmented nylon 6,6 indicates very little branching of the polymer chains, while an FBI of 0.62 indicates substantial branching, it can be concluded that both these polymers have modest branching. Depending on the level of branching desired, adjustments to the polymer or process can then be made.

EXAMPLE 3

A nylon 6,6 polymer flake was again melted in a screw melter and transferred at 290° C. to a spinning machine. The FBI was calculated on-line as in the previous examples and determined to be 0.74. The polymer melt temperature was then reduced to 282° C. The FBI value for the polymer being transferred at this lower temperature increased to 0.84 indicating virtually no branching. In both cases the polymer temperature at the capillary was maintained at 290° C. indicating that the FBI change was attributable to changing rheology of the polymer caused by reduced branch content.

EXAMPLE 4

A first nylon 6,6 polymer flake was again melted in a crew-melter and transferred to a spinning machine as in previous examples. The FBI was calculated on-line as in previous examples and found to be 0.74, indicating a modest level of branching and/or impurities. A second polymer made using adipic acid having reduced levels of impurities was then introduced into the transfer line and the FBI was determined to be 0.78 indicating a reduced level of impurities and/or branching.

I claim:

1. An apparatus for determining the Flow Behavior Index of a molten polymer having at a controlled temperature along a prescribed path, comprising:
   (a) a capillary of known length and diameter in line with the prescribed path;
   (b) means for successively diverting more than one small quantity of the molten polymer from the path to the capillary;
   (c) means for successively moving each small quantity through the capillary at a different controlled rate and at a constant temperature;
   (d) means for measuring the pressure drop across the capillary at each controlled rate;
   (e) means for using the controlled rates, pressure drops, capillary length and diameter to calculate shear rate and shear stress;
   (f) means for comparing shear rate and shear stress to determine the Flow Behavior Index.

2. The apparatus of claim 1 wherein the means for measuring the pressure drop across the capillary at each controlled rate is a viscometer.

3. The apparatus of claim 2 wherein the means for moving each small quantity of the molten polymer through the capillary at a different controlled rate is a variable-speed drive connected to a pump.

* * * * *

UNITED STATES PATENT AND TRADEMARK OFFICE
CERTIFICATE OF CORRECTION

PATENT NO. : 5,014,545
DATED : May 14, 1991
INVENTOR(S) : Sundar M. Rao

It is certified that error appears in the above-identified patent and that said Letters Patent is hereby corrected as shown below:

Column 8:

Claim 1, line 2, change "having" to -- moving --

Signed and Sealed this

Eighth Day of September, 1992

*Attest:*

DOUGLAS B. COMER

*Attesting Officer*      *Acting Commissioner of Patents and Trademarks*